US00PP34961P2

(12) United States Plant Patent
Growns

(10) Patent No.: US PP34,961 P2
(45) Date of Patent: Jan. 31, 2023

(54) ***ANIGOZANTHOS* PLANT NAMED 'KPAUSP'**

(50) Latin Name: ***Anigozanthos* hybrid**
Varietal Denomination: KPAUSP

(71) Applicant: Digby Growns, Perth (AU)

(72) Inventor: Digby Growns, Perth (AU)

(73) Assignee: Botanic Gardens and Parks Authority

( * ) Notice: Subject to any disclaimer, the term of this patent is extended or adjusted under 35 U.S.C. 154(b) by 0 days.

(21) Appl. No.: 17/721,454

(22) Filed: Apr. 15, 2022

(51) Int. Cl.
*A01H 5/02* (2018.01)
*A01H 6/00* (2018.01)

(52) U.S. Cl.
USPC ..... Plt./362

(58) Field of Classification Search
USPC ..... Plt./362
CPC ..... A01H 5/02; A01H 5/00; A01H 6/00
See application file for complete search history.

(56) References Cited

PUBLICATIONS

Botanic Gardens & Parks Authority 2021, New Release Green and Gold Kangaroo Paw an Aussie Dream, retrieved from the Internet on May 23, 2022 at https://www.bgpa.wa.gov.au/about-us/information/news/2898-new-release-green-and-gold-kangaroo-paw-an-aussie-dream, 2pp. (Year: 2021).*
Garden Express retrieved from the internet on May 23, 2022 at https://www.gardenexpress.com.au/product/bush-gems-celebrations-aussie-spirit-kangaroo-paw/, 6 pp. (Year: 2022).*
CPVO Register Version 4.2.27, retrieved on Aug. 24, 2022 at https://online.plantvarieties.eu/publicConsultationDetails?registerId=20221191&denomination=kpausp, 3 pp. (Year: 2022).*

* cited by examiner

*Primary Examiner* — June Hwu
(74) *Attorney, Agent, or Firm* — Cassandra Bright

(57) ABSTRACT

A new and distinct cultivar of *Anigozanthos* plant named 'KPAUSP' is disclosed, characterized by a distinctive very strongly reflexing perianth lobes. Ovaries and the lower perianth tube are covered in yellow hairs, pedicels covered in Red-Purple 59B hairs. The new variety is a *Anigozanthos*, typically produced as a garden or container plant.

2 Drawing Sheets

Latin name of the genus and species: *Anigozanthos* hybrid.

Variety denomination: 'KPAUSP'.

BACKGROUND OF THE INVENTION

The new cultivar is a product of a planned breeding program. The new variety originated as the result of a self-pollination made during 2015 of the parent, an unpatented, proprietary *Anigozanthos* referred to as '20121100'. 'KPAUSP' was discovered and selected by the inventor at a research greenhouse in New South Wales, Australia during 2016.

Asexual reproduction of the new cultivar 'KPAUSP' was New South Wales, Australia at a research laboratory by tissue culture during 2017. 'KPAUSP' has since produced several generations and has shown that the unique features of this cultivar are stable and reproduced true to type.

SUMMARY OF THE INVENTION

The cultivar 'KPAUSP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KPAUSP'. These characteristics in combination distinguish 'KPAUSP' as a new and distinct *Anigozanthos* cultivar:

1. Yellow hairs on ovaries and lower perianth tube.
2. Very strongly reflexing perianth lobes.
3. Red pedicel hairs.

PARENTAL COMPARISON

Plants of the new cultivar 'KPAUSP' are comparable to the parent in most horticultural characteristics; however, the new variety 'KPAUSP' differs in the following:

1. The new variety produces a yellow perianth tube color, while the seed parent produces a purple and cream perianth tube with orange ovary.

COMMERCIAL COMPARISON

Plants of the new cultivar 'KPAUSP' are comparable to the commercial *Anigozanthos* variety 'Green Dragon', unpatented. The two *Anigozanthos* varieties are similar in most horticultural characteristics; however, the new variety 'KPAUSP' differs in the following:

1. The new variety has very strongly reflexing perianth lobes, while this comparator has strongly reflexing perianth lobes.
2. Ovary hair color of the new variety is yellow, while the ovary hair color of this comparator is green.
3. Pedicel hair color of the new variety is red, while the pedicel hair color of this comparator is green.
4. Leaf length of the new variety is shorter than the leaf length of this comparator.

BRIEF DESCRIPTION OF THE PHOTOGRAPHS

Figure 1:
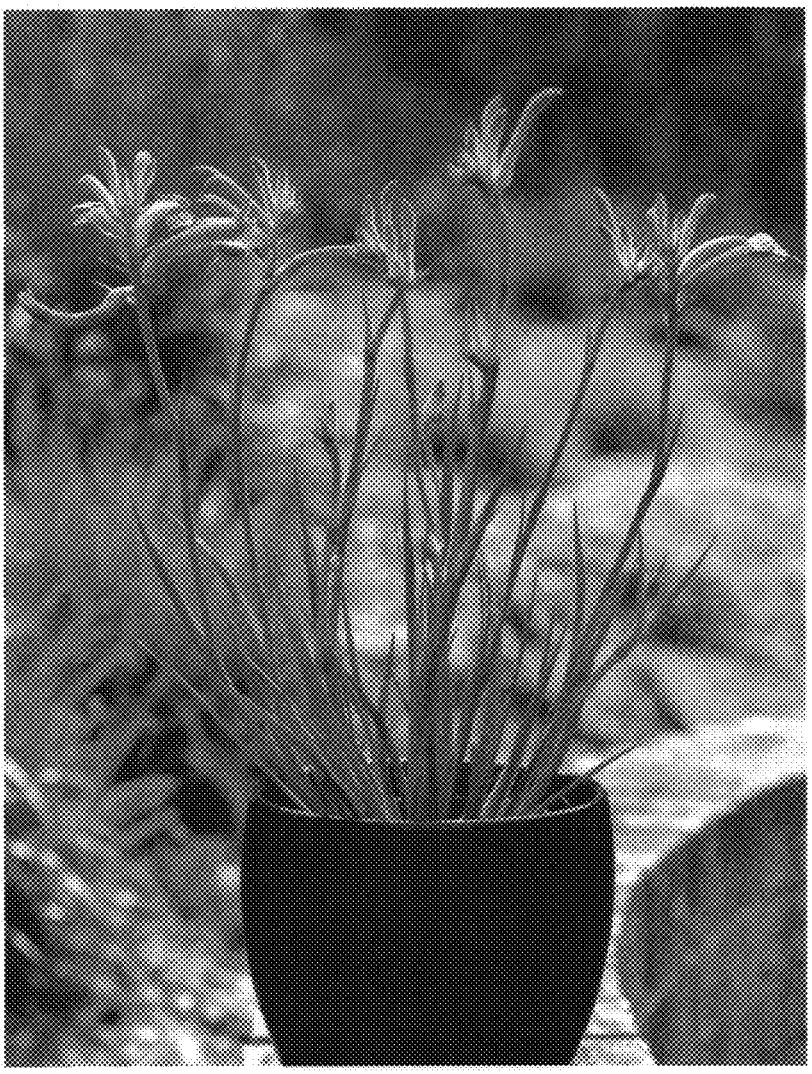

The accompanying photograph in FIG. 1 illustrates in full color a typical plant of 'KPAUSP' grown outdoors in Kangy Angy, NSW, Australia. This plant is approximately 16 weeks old, shown in a 14 cm pot.

Figure 2:
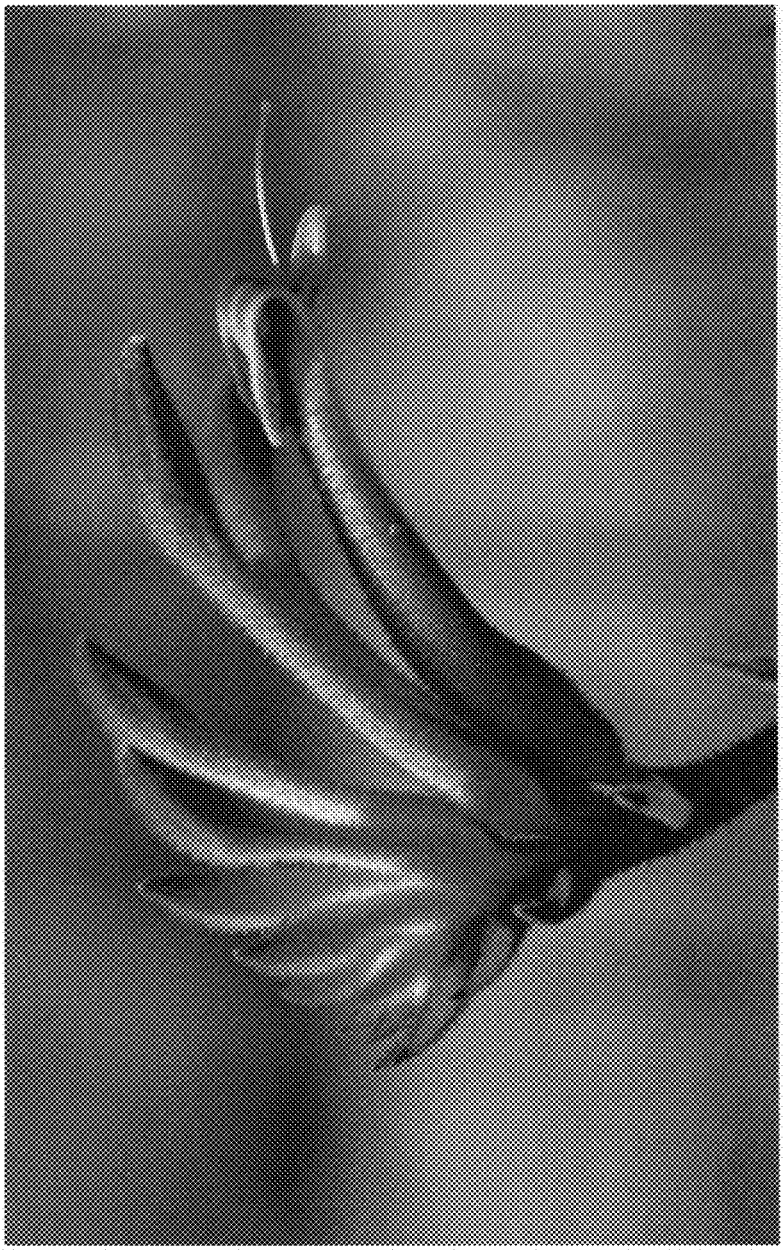

FIG. 2 illustrates a close-up view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, 2015, except where general terms of ordinary dictionary significance are used. The following observations and measurements describe 'KPAUSP' plants grown outdoors in full sun in Kangy Angy, NSW, Australia. Temperatures ranged from 20° C. to 32° C. during the day and 5° C. to 15° C. at night. No artificial light, photoperiodic treatments or chemical treatments were given to the plants. Measurements and numerical values represent averages of typical plant types.

Botanical classification: *Anigozanthos* hybrid 'KPAUSP'.

PROPAGATION

Time to initiate roots: 10 to 21 days at approximately 22° C. to 24° C.

Time for produce a rooted liner: 28 to 36 days at approximately 24° C. to 26° C.

PLANT

Age of plant described: Approximately 16 weeks from a rooted plantlet

Growth habit: Compact upright fan shaped perennial with basal only branching.

Pot size: 14 cm.

Plant type: Compact upright flowering perennial.

Plant habit: Upright growing stems emerge basally.

Plant spread: Approximately 30 cm.

Height:

- *Top of foliar plane.*—22 cm.
- *Top of flowering plane.*—35 cm.

Growth Rate: Moderate

Description of roots (general thickness, color, vigor, production characteristics): Thick fleshy, main roots with fine hairs and a fibrous network of smaller roots. Colored near RHS 155B Yellowish White and 164B Moderate orange yellow.

FOLIAGE

Leaf:

- *Arrangement.*—Basally emerging, irregular rosette. Primarily fan-shaped.
- *Average length.*—22 cm.
- *Average width.*—Approximately 5 mm.
- *Shape of blade.*—Subulate.
- *Apex.*—Acuminate.
- *Base.*—Clasping
- *Attachment.*—Sessile.
- *Margin.*—Entire.
- *Leaf attitude.*—Erect.
- *Texture of top surface.*—Glabrous.
- *Texture of lower surface.*—Glabrous.
- *Appearance of top surface.*—Smooth, leathery with slight shine.
- *Appearance of bottom surface.*—Smooth, leathery with slight shine.
- *Color.*—Young foliage upper side: RHS Green N138B. Young foliage under side: RHS Green N138B. Mature foliage upper side: RHS Green N138A. Mature foliage under side: RHS Green N138A.
- *Venation.*—Type: Parallel. Venation color upper side: Near RHS Green 139A. Venation color under side: Near RHS Green 139A.
- *Petiole.*—Not Present.

FLOWER

Natural flowering season: Freely flowering under outdoors growing conditions with substantially continuous blooming from Spring through Autumn.

Inflorescence and flower type and habit: Ramification not present. Large flowers arranged singly on terminal racemes. Individual flowers are zygomorphic, tubular, with a curved perianth.

Inflorescence height: Approximately 4.5 cm.

Inflorescence width: Approximately 6 cm.

Flower longevity on plant: Individual flowers last approximately 25 days.

Approximate quantity of flowers per plant: About 12 inflorescences per plant. Each inflorescence has 5 to 6 open flowers and 5 to 6 flower buds.

Persistent or self-cleaning: Persistent.

Bud:

- *Shape.*—Tubular.
- *Length.*—About 1 cm.
- *Diameter.*—About 6 mm.
- *Texture.*—Highly pilous.
- *Color.*—Near RHS Yellow 2C, strongly flushed Green 135C.

Flower size:

- *Diameter.*—Approximately 4.0 cm (apical section open).
- *Length.*—Approximately 6.5 cm.

Petals (unfused floral section):

- *Length.*—Approximately 0.8 cm.
- *Diameter.*—Approximately 0.5 cm
- *Quantity.*—6.
- *Texture.*—Exterior covered in dense, pilous hairs. Interior glabrous.
- *Apex.*—Acute.
- *Color.*—When opening: Outer, visible surface: RHS Green N134A. Fully opened: Outer surface: RHS Green N134A. Inner surface: RHS Yellow Green 144B.

Perianth tube:

- *Length.*—Approximately 4.5 cm.
- *Diameter.*—Approximately 6 mm.
- *Texture.*—Outer texture highly pubescent, inner texture glabrous.
- *Description.*—Very strongly flared distally.
- *Color.*—When opening: Outer, visible surface, including perianth hair color: Lower half of perianth tube is Yellow 2B. Upper half is Green N134A. Fully opened: Outer surface, including perianth hair color:

Lower half of perianth tube is 2B Brilliant greenish yellow. Upper half is N134A. Inner surface: RHS Yellow Green 144B Floral bracts:

*Quantity.*—8.

*Shape.*—Narrow deltoid.

*Tip.*—Acuminate.

*Base.*—Clasping.

*Texture.*—Pilous on lower surface, glabrous on upper surface.

*Length.*—Approximately 4 cm.

*Width.*—Approximately 4 mm.

*Color.*—Upper surface: RHS Green 143B. Lower surface: RHS Green N138A with Red-Purple 59B hairs.

Peduncle:

*Length.*—8 cm.

*Diameter.*—5 mm.

*Color.*—RHS Green N138A covered in Red-Purple 59B hairs.

*Aspect.*—Straight.

*Strength.*—Very strong.

*Texture.*—Pilous.

Pedicels:

*Length.*—Average 6 mm.

*Diameter.*—2 mm.

*Color.*—Near RHS Yellow 2B. Tips of hair turn Red-Purple 59B as flower matures.

*Orientation.*—Approximately 45 degrees from peduncle.

*Strength.*—Very strong.

*Texture.*—Pilous.

Sepals not Present.

Nectaries not observed.

Fragrance: None.

REPRODUCTIVE ORGANS

Androecium

Stamens:

*Number.*—6.

Anthers:

*Quantity at top of perianth.*—6.

*Shape.*—Ovoid.

*Length.*—Approximately 5 mm.

*Color.*—RHS Yellow-Green 144A.

*Pollen.*—Color: RHS Yellow 11A. Quantity: Moderate.

Gynoecium:

Pistil:

*Number.*—1.

*Length.*—4.8 cm.

*Style.*—Length: 1 cm. Color: RHS Yellow-Green 144A.

*Stigma.*—Shape: Circular 0.1 cm. Color: RHS Yellow-Green N144B. Ovary Color: RHS Yellow 2B. Tips of hairs mature to Red-Purple 59B as flowers open and mature.

OTHER CHARACTERISTICS

Seeds and fruits: Not observed to date.

Disease/pest resistance: Neither resistance nor susceptibility to the normal diseases and pests of *Anigozanthos* has been observed.

Temperature tolerance: From approximately 0° C. to more than 40° C.

What is claimed is:

1. A new and distinct cultivar of *Anigozanthos* plant named 'KPAUSP' as herein illustrated and described.

* * * * *